United States Patent [19]
Iwata et al.

[11] Patent Number: 6,019,728
[45] Date of Patent: Feb. 1, 2000

[54] CATHETER AND SENSOR HAVING PRESSURE DETECTING FUNCTION

[75] Inventors: Hitoshi Iwata; Koichi Itoigawa, both of Aichi-ken, Japan

[73] Assignee: Kabushiki Kaisha Tokai Rika Denki Seisakusho, Japan

[21] Appl. No.: 08/852,223

[22] Filed: May 6, 1997

[30] Foreign Application Priority Data

May 8, 1996 [JP] Japan .................................. 8-114005
May 8, 1996 [JP] Japan .................................. 8-114006

[51] Int. Cl.⁷ .......................................................... A61B 5/00
[52] U.S. Cl. ............................. 600/486; 600/505; 600/561
[58] Field of Search ..................................... 600/486, 488, 600/561, 505

[56] References Cited

U.S. PATENT DOCUMENTS

| | | | |
|---|---|---|---|
| 4,475,556 | 10/1984 | Reiff | 600/486 |
| 4,850,358 | 7/1989 | Millar | 600/486 |
| 5,113,868 | 5/1992 | Wise et al. | 600/486 |
| 5,207,227 | 5/1993 | Powers | 600/488 |
| 5,715,827 | 2/1998 | Corl et al. | 600/486 |

OTHER PUBLICATIONS

Borky et al, "Integrated Signal Conditioning for Silicon Pressure Sensors," IEEE Transactions on Electron Devices, vol. ED–26, No. 12 (Dec. 1979), pp. 1904–1910.

*Primary Examiner*—Robert L. Nasser
*Attorney, Agent, or Firm*—Quarles & Brady LLP

[57] ABSTRACT

A catheter includes a longitudinally extending catheter tube to be inserted into a body. A plurality of sensing portions are arranged in the catheter tube for detecting at least two types of pressures acting on the catheter when inserted into the body. Each sensing portion is arranged along the longitudinal direction of the catheter tube. A silicone gel transmits the two types of pressures acting in the body to each sensing portion. The two types of pressures act on each sensing portion in a radial direction of the catheter tube by way of the silicone gel.

15 Claims, 5 Drawing Sheets

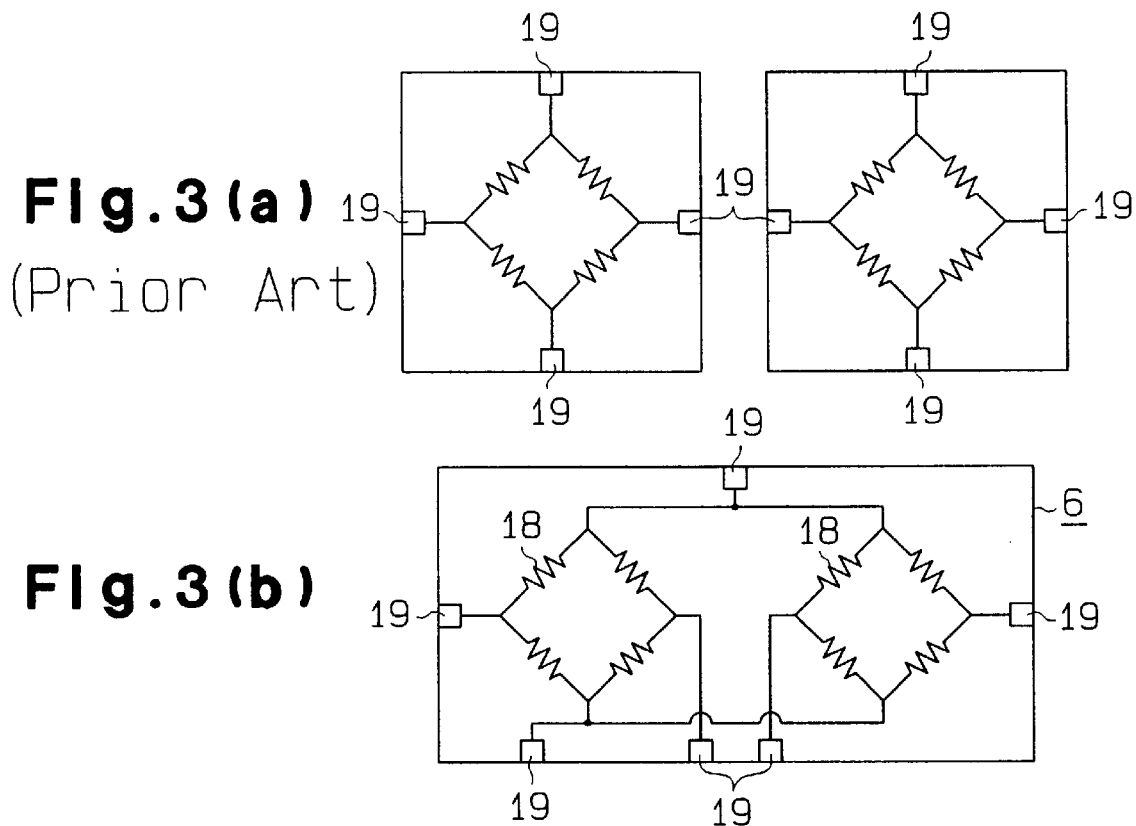
Fig.3(a) (Prior Art)
Fig.3(b)
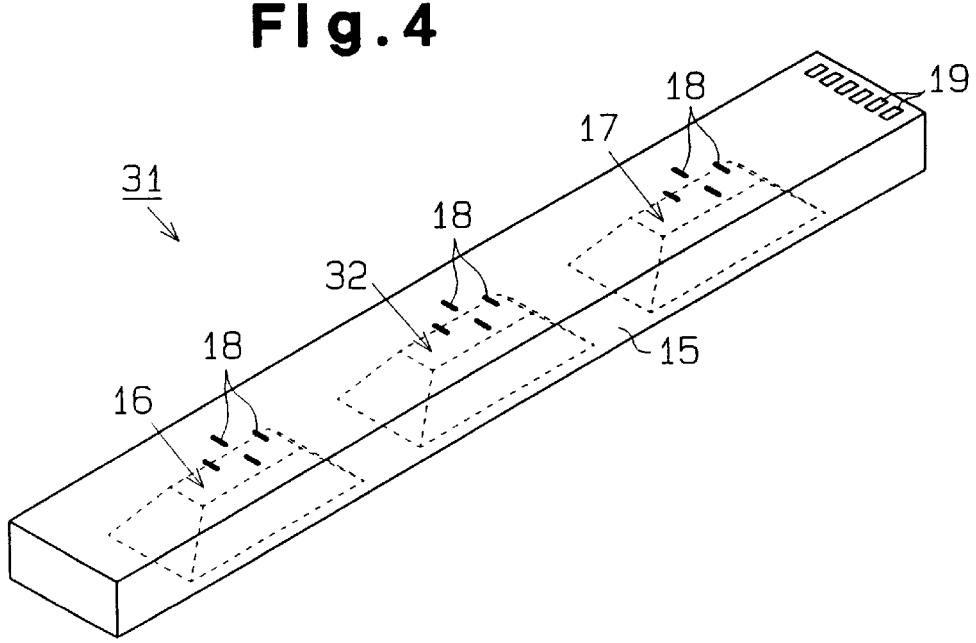
Fig.4

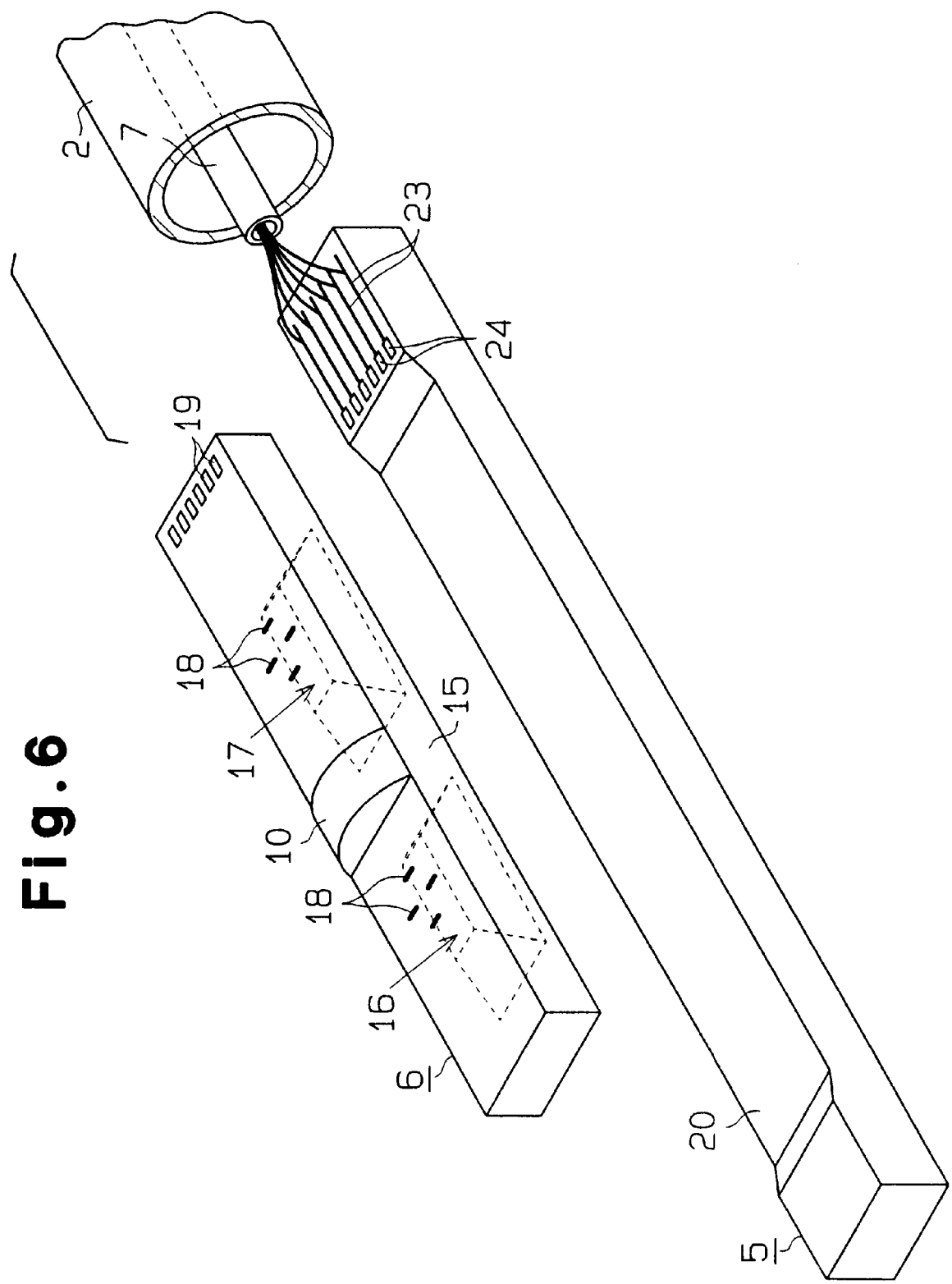

CATHETER AND SENSOR HAVING PRESSURE DETECTING FUNCTION

BACKGROUND OF THE INVENTION

The present invention relates to catheters, and more particularly, to catheters capable of detecting pressure applied to the distal end thereof when inserted into a body. The present invention further relates to semiconductor type sensors employed in such catheters.

There are catheters that are inserted into various body vessels, such as blood vessels, to measure blood pressure. In the prior art, this type of catheter cannot detect the state of the vessel in front of the catheter tube with respect to its advancing direction. Thus, operators have had to depend on their senses to manipulate the catheter tube. Therefore, experience is required to guide the distal end of the catheter tube to a desired region in the body.

To solve the above problem, a catheter having a catheter tube provided with a sensing mechanism to detect obstacles at its distal end has been proposed. The catheter tube is manipulated based on the sensing results.

In the catheter provided with the sensing mechanism, a distal portion of the catheter tube is partitioned into a first chamber and a second chamber by a pressure partition. The first chamber is located at the distal end. The first chamber receives a semiconductor type pressure sensor chip for detecting obstacles and is filled with a pressure transmitting medium such as silicone gel. A tap seals an opening of the catheter tube.

The second chamber located at the proximal side of the catheter tube receives a seat and two semiconductor type pressure sensor chips, which are mounted on the seat to detect blood pressure. The chamber is also filled with a pressure transmitting medium such as silicone. The two sensor chips are each provided with a bonding pad and are connected to a signal cable. Obstacle detection signals and blood pressure detection signals produced by the sensor chips are outputted via the signal cables.

However, in the above catheter, an obstacle detecting sensor chip is provided in addition to a blood pressure detecting sensor chip. This necessitates a large space for receiving the sensor chips. Furthermore, signal cables must be connected to each sensor chip. This enlarges the distal portion of the catheter having the sensor mechanism. In addition, the structure of the catheter is complicated and its assembly is troublesome.

SUMMARY OF THE INVENTION

Accordingly, it is an objective of the present invention to provide a catheter having a sensor that allows the size of the distal portion diameter to be minimized by providing a sensor having a compact and simple distal end structure.

Furthermore, it is another objective of the present invention to provide an optimal physical quantity sensor for the above catheter.

To achieve the above objectives, a physical quantity sensor according to a first embodiment of the present invention includes a hollow support member and a plurality of sensing portions arranged in the support member. The sensing portions detect at least two a physical characteristics external to the support member. The sensing portions are arranged along the longitudinal direction of the support member. The sensor has means to transmit the at least one of the characteristics to each sensing portion. The physical quantity is applied to each sensing portion in a radial direction of the support member through the transmitting means.

A catheter according to a second embodiment of the present invention includes a longitudinally extending tube for insertion into the body. A plurality of sensing portions are arranged in the catheter tube to detect at least two physical characteristics external to the tube. Each sensing portion is arranged along the longitudinal direction of the catheter tube. The catheter includes means to transmit a pressure representing one of the two physical characteristics to each sensing portion. The pressure is applied to each sensing portion in a radial direction of the catheter tube through the transmitting means.

BRIEF DESCRIPTION OF THE DRAWINGS

The features of the present invention that are believed to be novel are set torth with particularity in the appended claims. The invention, together with objects and advantages thereof, may best be understood by reference to the following description of the presently preferred embodiments together with the accompanying drawings in which:

FIG. 3(a) is a schematic diagram illustrating dispersion strain gauges of a prior art sensor chip;

FIG. 3(b) is a schematic diagram illustrating dispersion strain gauges of a sensor chip according to the present embodiment;

FIG. 4 is a perspective view showing a sensor chip according to a modification of the first embodiment;

FIG. 6 is an exploded perspective view showing a sensor chip, a seat, a pressure partition, and a catheter tube employed in the catheter of FIG. 5.

DETAILED DESCRIPTION OF THE PREFERRED EMBODIMENTS

Figure 1:
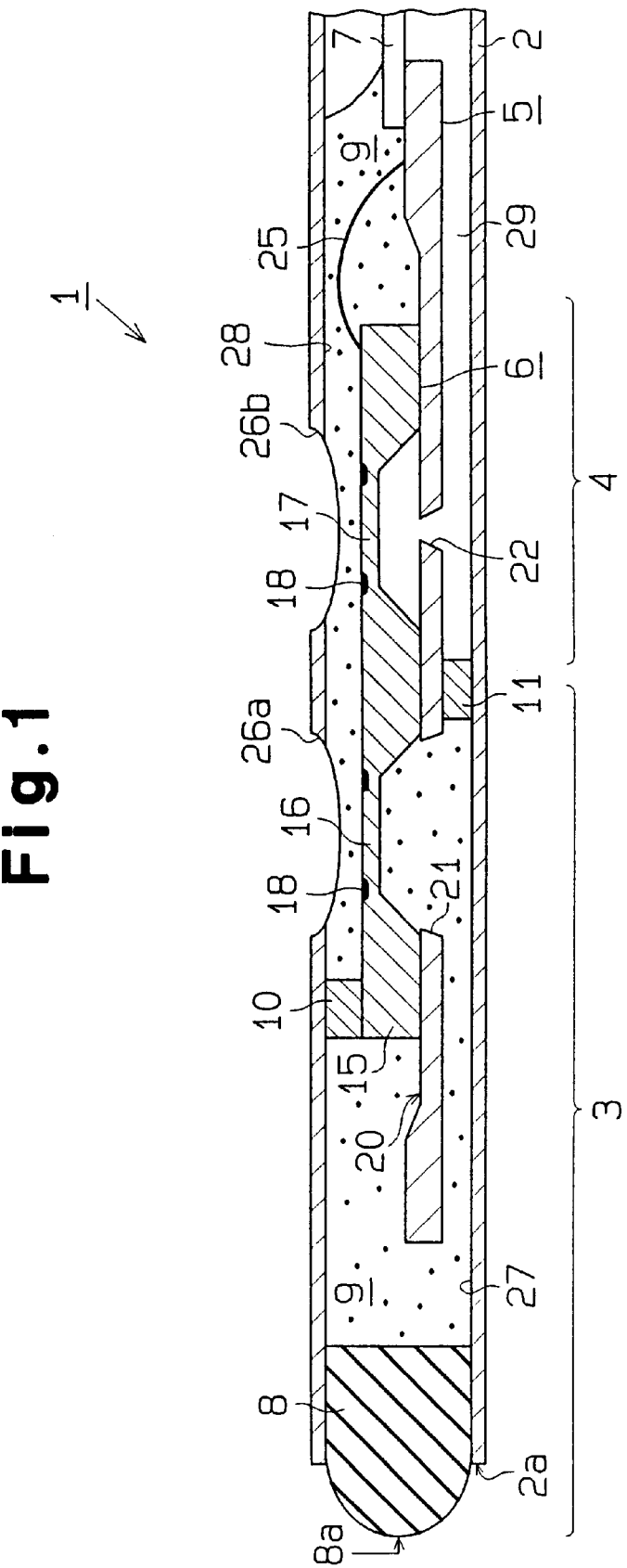
FIG. 1 is a cross-sectional view showing a first embodiment of a sensor assembly mounted on the distal end of a catheter according to the present invention.

A first embodiment of a blood vessel catheter 1 according to the present invention will now be described with reference to FIGS. 1 to 3. The blood vessel catheter 1 includes a catheter tube 2, which is inserted into a blood vessel, and a manipulating device (not shown), which is arranged at the basal portion of the tube 2 to operate the catheter 1 from outside the body. When operating the catheter 1, the distal end of the catheter 1 is guided to, for example, a narrowed region of the blood vessel using the manipulating device. Air is then supplied through an air pipe (not shown) arranged in the tube 2 to expand a balloon (not shown). This enlarges the narrowed region of the blood vessel from its inner side.

The catheter 1 includes a cap 8 that seals an opening 2a defined at the distal end of the catheter tube 2 and slides in accordance with the forces and pressure applied to a receiving portion 8a defined at its outer portion. The cap 8 is made of biocompatible resin materials such as PTFE (polytetrafluoroethylene) and vinyl chloride. Biocompatibility means that the reactivity with respect to blood, body fluids, lymph, and other biological substances is low.

A sensor assembly having an obstacle sensing portion 3 and a blood pressure sensing portion 4 is provided at the distal end of the catheter tube 2. The sensor assembly includes a seat 5, a signal cable 7, the cap 8, a pressure transmitting medium 9, and pressure partitions 10, 11. The sensor assembly further includes a semiconductor type physical quantity sensor chip 6, as shown in FIG. 2. In this embodiment, the physical quantity is pressure, which represents to the forces and pressure applied to the catheter. Accordingly, the semiconductor type physical quantity sensor chip 6 will hereinafter be referred to as a pressure sensor chip, or sensor chip 6. The pressure sensor chip 6 is provided with a silicon substrate 15.

The silicon substrate 15 and tho seat 5 are each rectangular. The shorter sides of the silicon substrate 15 and the seat 5 are substantially equal to the inner diameter of the tube 2. The longer sides of the silicon substrate 15 and the seat 5 are at least greater than the inner diameter of the tube 2.

The pressure sensor chip 6 is mounted on the seat 5, and accommodated in the catheter tube 2. Plate-like first and second sensing portions 16, 17 for sensing pressure fluctuations in the blood vessels are formed by etching the bottom surface of the silicon substrate 15. The sensing portions 16, 17 are arranged along the axis of the tube 2 with a predetermined interval therebetween.

Each sensing portion 16, 17 is provided with four dispersion strain gauges 18, which are arranged on the top surface of the substrate 15. Six bonding pads 19 are arranged on the top surface of the basal shorter side of the substrate 15 (to the right as viewed in FIG. 1). The bonding pads 19 and the dispersion strain gauges 18 are connected to one another by a wiring pattern (not shown) provided on the top surface of the substrate 15. FIG. 3(b) diagrammatically shows the connection between the bonding pads 19 and the dispersion strain gauges 18. Each gauge 18 is represented by a resistor symbol.

With the pressure sensing chip 6 and the seat 5 accommodated in the tube 2, the first sensing portion 16 is located toward the distal end of the tube 2 (to the left as viewed in FIG. 1). The second sensing portion 17 is located toward the basal end of the tube 2 (to the right as viewed in FIG. 2). Furthermore, the sensing portions 16, 17 are arranged substantially parallel to the axis of the tube 2.

Figure 2:
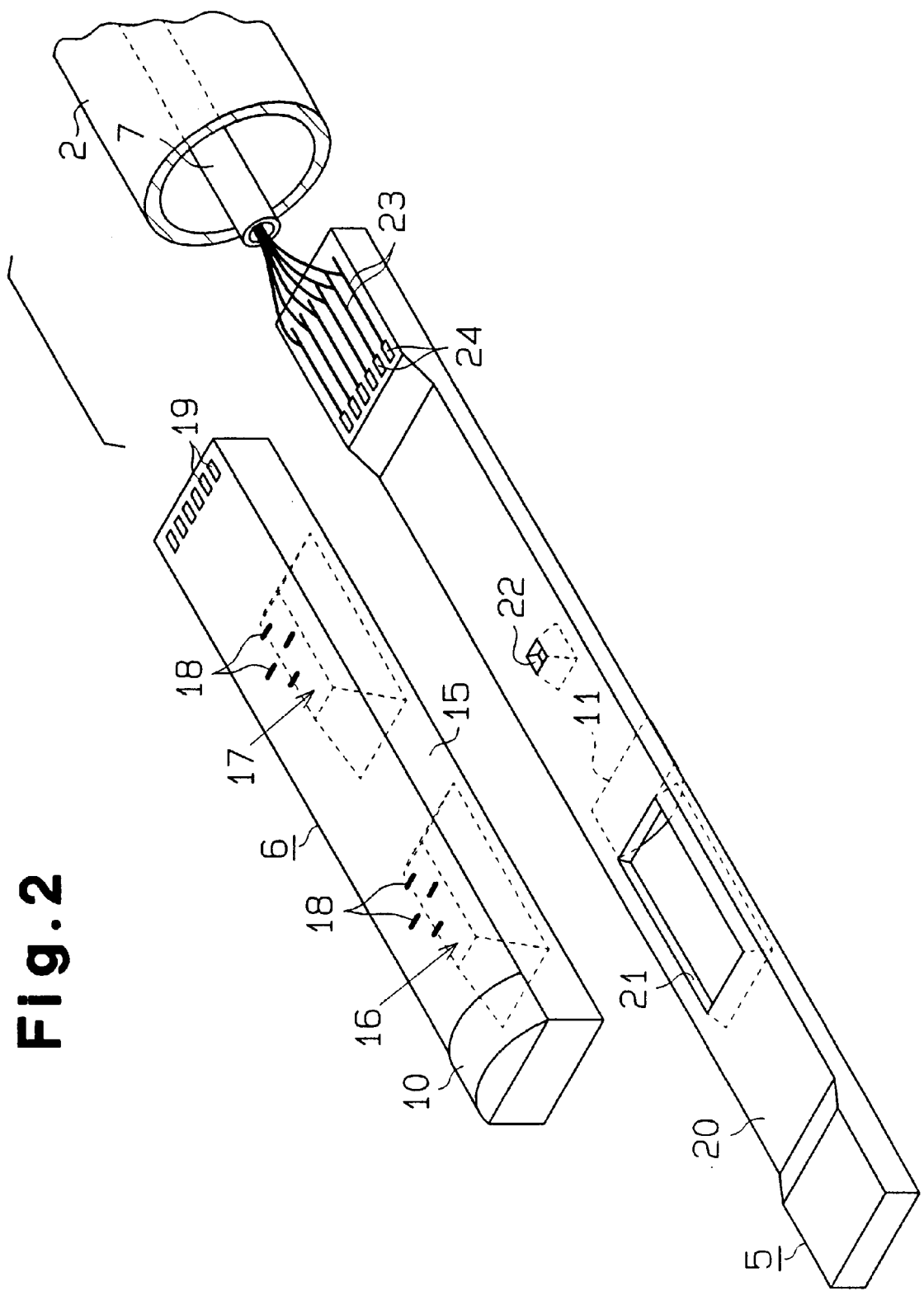
FIG. 2 is an exploded perspective view showing a sensor chip, a seat, a pressure partition, and a catheter tube that are employed in the catheter of FIG. 1.

The seat 5 as shown in FIGS. 1 and 2 is made of silicon and has a recess 20 defined in its upper middle portion to mount the sensor chip 6 thereon. A first through hole 21 and a second through hole 22 extend through the recess 20. The first through hole 21 is located directly below the first sensing portion 16, while the second through hole 22 is defined directly below the second sensing portion 17.

As shown in FIG. 2, a plurality of straight wiring patterns 23 are provided on the top surface of the basal portion of the seat 5. A bonding pad 24 is provided at the distal end of each wiring pattern 23. The bonding pads 24 of the seat 5 and the bonding pads 19 of the sensor chip 6 are electrically connected to one another by bonding wires 25, which are shown in FIG. 1. Furthermore, the lead wires of the signal cable 7 are soldered to the proximal ends of the wiring patterns 23. The signal cable 7 is connected to the manipulating device (not shown) through the tube 2.

A substantially semi-cylindrical pressure partition 10 is provided on the distal top surface of the sensor chip 6. In the same manner, a substantially semi-cylindrical pressure partition 11 is provided on the bottom middle surface of the seat 5. The pressure partitions 10, 11 seal the space between the seat 5 and the inner wall surface of the tube 2 and the space between the sensor chip 6 and the inner wall surface of the tube 2. The pressure partitions 10, 11 cooperate with the seat 5 and the sensor chip 6 to divide the inner space at the distal portion of the tube 1 into first and second inner spaces 27, 28.

As shown in FIG. 1, two pressure communicating holes 26a, 26b, which are spaced from each other, are provided in the wall of the catheter tube 2 to communicate the ambient pressure of the tube 2 into the interior of the tube 2. The pressure communicating holes 26a, 26b are opposed to the top surface of the sensing portions 16, 17.

The first inner space 27 is filled with a silicone gel 9, which serves as biocompatible pressure transmitting medium. The silicone gel 9 is filled into the bottom side of the first sensing portion 16 through the first through hole 21. The silicone gel 9 is further filled into the second inner space 28 and surrounds the top surfaces of the first and second sensing portions 16, 17. The gel 9 also surrounds the connection between the cable 7 and the seat 5. Although the silicone gel 9 is exposed externally through the pressure communicating holes 26, the elasticity of the silicone gel 9 keeps the gel 9 within the second inner space 28. Thus, the gel 9 does not leak out through the holes 26a, 26b.

The space at the bottom side of the second sensing portion 17 communicates with a hollow area 29, which is located at the basal side of the sensor assembly, through a back pressure hole, or the second through hole 22. The hollow area 29 is not filled with the silicone gel 9 and is communicated with the exterior of the tube 2. Therefore, the pressure in the hollow space 29 is equal to the atmospheric pressure.

The sensing operation of the catheter 1 of this embodiment will now be described.

When the catheter 1 is inserted into a blood vessel, the pressure in the blood vessel, or the blood pressure, acts on the bottom surface of the first sensing portion 16 by way of the pressure receiving surface 8a of the cap 8 and the silicone gel 9. The blood pressure also acts on the top surface of the first sensing portion 16 through the silicone gel 9 within the pressure communicating hole 26a. Furthermore, the blood pressure acts on the top surface of the second sensing portion 17 by way of the silicone gel 9 within the pressure communicating hole 26b. Atmospheric pressure acts on the bottom surface of the second sensing portion 17 through the hollow area 29 and the hole 22.

The strain applied to first and second sensing portions 16, 17 changes in accordance with fluctuations of the pressure acting on the top and bottom surfaces of the sensing portions 16, 17. This fluctuates the resistance valve of the strain gauges 18. The sensor chip 6 outputs electrical signals to the seat 5 through the bonding wire 25 based on fluctuations of the resistance value of the strain gauges 18.

When there are no obstacles (thrombus or tumor) or narrowed region in the blood vessel, the same gel pressure, which represents blood pressure, acts on both top and bottom surfaces of the first sensing portion 16. Thus, there is substantially no strain acting on the first sensing portion 16. Accordingly, the first sensing portion 16 outputs a signal indicating that there are no obstacles. Furthermore, the second sensing portion 17 outputs a signal corresponding to the blood pressure, which has been corrected using the atmospheric pressure.

When the cap 8 comes upon an obstacle or narrowed region in the blood vessel as the catheter 1 is further advanced, the inserting resistance acting on the tube 2 increases. The obstacle or narrowed region acts on the receiving surface 8a of the cap 8, and the pressure of the silicone gel 9 in the first inner space 27 increases. This increases the pressure acting on the bottom surface of the first sensing portion 16. Accordingly, the first sensing portion 16 outputs a signal indicating the presence of an obstacle or the like.

During the output of the signal indicating the presence of an obstacle or the silicon gel pressure representing the blood pressure acts on the top and bottom surfaces of the first sensing portion 16. Accordingly, changes caused by the pulsation of the blood pressure are canceled from the obstacle detection signal.

The obstacle detection signals and the blood pressure signals are input into an electrical circuit of the manipulating device arranged at the basal end of the tube 2 by way of the bonding wire 25, the wiring patterns 23, and the signal cable 7. The signals are processed in the electric circuit and visualized. This enables the operator to confirm the blood pressure through the visualized data. Furthermore, the operator may confirm the state in front of the catheter, that is, the presence of obstacles or narrowed regions may be confirmed. When obstacles or the like are detected, the operator may manipulate a wire to shift the distal end of the sensor assembly toward a direction in which the pressure decreases.

The following effects are also obtained through this embodiment.

Among the two sensing portions 16, 17 of the sensor chip 6 in the catheter 1, the first sensing portion 16 is used to detect obstacles, while the second portion 17 is used to detect the blood pressure. Therefore, multiple types of sensing operations may be performed by the single sensor chip 6.

In this case, some of the bonding pads 19 on the sensor chip 9 and part of the cable 7 may share common parts. More specifically, prior art catheters are provided with a sensor chip for each of the two detected characteristics. Therefore, a total of eight bonding pads 19 are necessary (FIG. 3(a)). In contrast, this embodiment requires only six bonding pads (FIG. 3(b)). As a result, the sensor chip 6 is more compact. This enables the accommodating space to be reduced. Furthermore, it is not necessary to provide a signal cable for each sensor chip. This allows the diameter of the catheter to be reduced and simplifies the structure and assembly of the catheter.

The sensor chip 6 is rectangular and arranged in the tube 2 so that its longitudinal direction is parallel to the axis of the tube 2. Therefore, the sensor chip 6 can be received in the tube 2 even if the surface area of the sensor chip 6 is greater than the cross-sectional area of the catheter tube 2. By arranging the first and second sensing portions 16, 17 along the longitudinal direction of the tube 2, the width of the sensor chip 6 can be decreased. This contributes to the reduction of the diameter of the sensor assembly.

The dispersion strain gauges 18 are provided on each sensing portion 16, 17. This allows secure and fine formation of the gauges 18 through semiconductor processes known in the prior art. Thus, the technical difficulties associated with the production of the sensor chip 6 are small.

In this embodiment of the catheter 1, accurate obstacle detection signals and blood pressure detection signals, from which fluctuation elements such as the blood pressure and the atmospheric pressure have been excluded, are obtained. Furthermore, the pressure partitions 10, 11 prevent the interference of pressure between the obstacle detecting section and the blood pressure detecting section. This positively enhances the accuracy of sensing both obstacles and blood pressure.

The bonding pads 19 are concentrated at the end portion of the silicon substrate 15. This facilitates coupling of the silicon substrate 15 to the seat 5 and saves space.

The present invention is not limited to the above embodiment and may be modified as described below.

The sensor chip 6 may include three or more sensing portions. For example, in a further embodiment shown in FIG. 4, a sensor chip 31 includes three sensing portions 16, 17, 32 arranged linearly along the longitudinal direction of the sensor chip 31. In such case, the third sensing portion 32 may be used to sense a physical quantity other than pressure fluctuations, which are caused by obstacles, and blood pressure. The third sensing portion 32 may also be used as a back-up for the first or second sensing portions 16, 17.

The sensing portions of the sensor chips 6, 31 may be cantilevered. Furthermore, the sensing portions of the sensor chips 6, 31 may be used to sense physical characteristics other than force and pressure such as acceleration, temperature, and magnetism. The sensing portions provided in a single sensor chip 6, 31 may be used to detect the same type of physical quantity, as in the above embodiments, or may be used to detect different types of physical quantities.

The external connecting terminals are not limited to the bonding pads 19. Pins or other fattening means may be used. The pressure partitions 10, 11 may be formed integrally with the sensor chips 6, 31 or the seat 5. Furthermore, the pressure partitions 10, 11 may be formed to project from the inner circumferential surface of the catheter tube 2.

The seat 5 may be eliminated. In such case, the size of the catheter tube 2 is further reduced by the reduced volume of the seat 5. Furthermore, elongated containers other than the catheter tube 2 may be used to accommodate the sensor chips 6, 31.

A further embodiment according to the present invention will now be described with reference to FIGS. 5 and 6. Particularly, parts differing from the first embodiment shows in FIG. 1 will be described. Furthermore, to avoid a redundant description, like or same reference numerals are given to those components that are like or the same as the corresponding components of the first embodiment.

Figure 5:
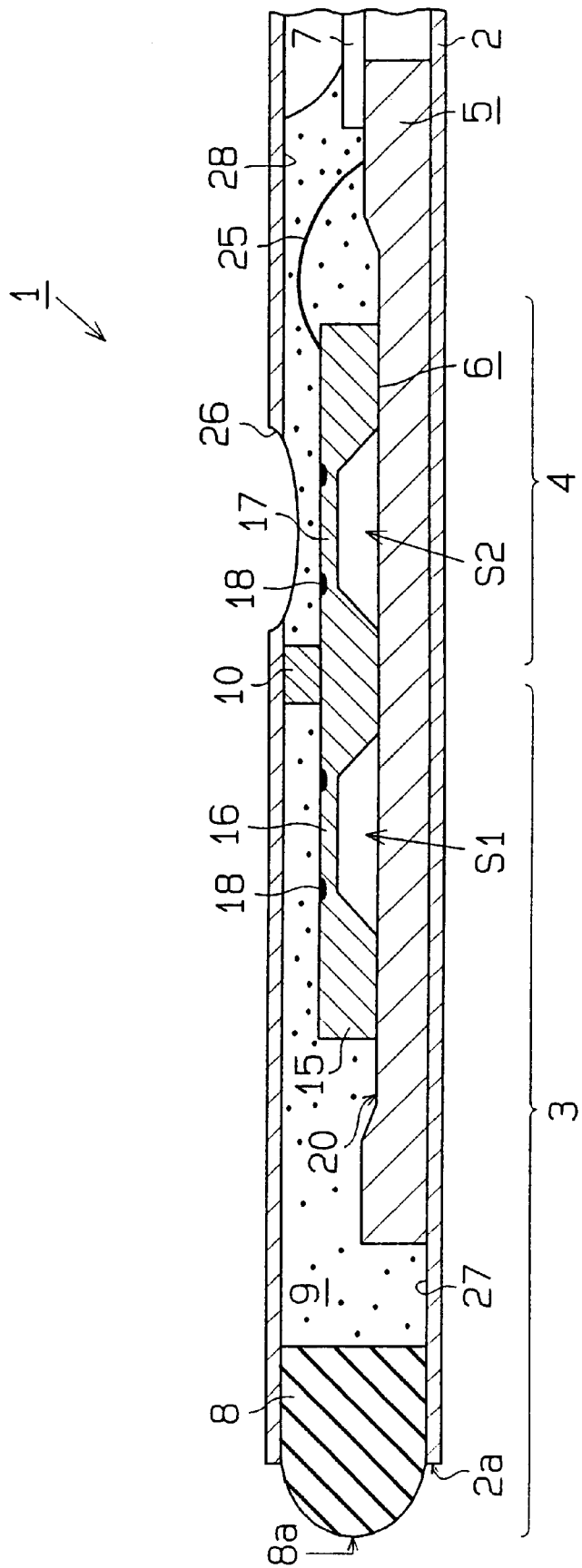
FIG. 5 is a cross-sectional view showing a sensor assembly provided at the distal end of a catheter according to a second embodiment of the present invention.

As shown in FIGS. 5 and 6, the seat 5 of this embodiment is made of a solid silicon body and has a recess 20 defined on the top surface of the seat 5 to receive the sensor chip 6. The sensor chip 6 is secured to the recess 20 of the seat 5. A first pressure reference chamber S1 is defined between the first sensing portion 16 and the seat 5, while a second pressure reference chamber S2 is defined between the second sensing portion 17 and the seat 5. The pressure reference chambers S1, S2 are separated from the surrounding space.

A substantially semi-cylindrical pressure partition 10 is provided on the top surface of the sensor chip 6 between the first sensing portion 16 and the second sensing portion 17. The pressure partition 10 seals space defined between the sensor chip 6 and the inner surface of the tube 2 and partitions interior of the tube 2 into the first and second inner spaces 27, 28.

As shown in FIG. 5, a pressure communicating hole 26 extends through the wall of the catheter tube 2 to communicate the ambient pressure of the tube 2 into the tube 2. The pressure communicating hole 26 is arranged at a position opposed to the second sensing portion 17.

The first and second inner spaces 27, 28 are filled with the silicone gel 9, which serves as a biocompatible pressure transmitting medium. The silicone gel 9 filled in the first inner space 27 surrounds the top surface of the first sensing portion 16. Furthermore, the silicone gel 9 filled in the second inner space 28 is exposed from the pressure communicating hole 26 and surrounds the entire top surface of the second sensing portion 17. The silicone gel 9 further encompasses the connection between the signal cable 7 and the seat 5.

In the catheter 1 of the above structure, the pressure acting on the pressure receiving portion 8a of the cap 8 increases if an obstacle or a narrowed region exists in the blood vessel of the insertion passage. The pressure fluctuation is transmitted to the top surface of the first sensing portion 16 by way of the silicone gel 9. This increases the strain acting on the first sensing portion 16 and causes changes in the resistance value of the strain gauges 18 arranged thereon.

The sensor chip 6 outputs electric signals, which correspond to the changes in the resistance value of the strain gauges 18 on the first sensing portion 16, to the seat 5 by way of the bonding wire 25. The output signals, or obstacle detection signals, use the pressure in the pressure reference chamber S1 as a reference. The obstacle detection signals are transmitted to the electric circuit 17 of the manipulating device of the catheter through the signal cable 7.

Fluctuations in blood pressure are transmitted to the top surface of the second sensing portion 17 by way of the pressure communicating hole 26 and the silicone gel 9. The second sensing portion 17 is strained in accordance with the blood pressure, and the resistance values of the strain gauges 18 arranged thereon change accordingly. The second sensing portion 17 outputs electric signals to the seat 5 through the bonding wire 25. The output signals, or blood pressure signals, use the pressure in the pressure reference chamber S2 as a reference. The blood pressure signals are further transmitted to the electric circuit of the manipulating device through the signal cable 7.

The blood pressure signals transmitted to the electric circuit are visualized without performing any computations. The obstacle detection signals are visualized after performing the following computation. In the computations, the waveform corresponding to the blood pressure detection signal is subtracted from a waveform corresponding to the obstacle detection signal. The computation eliminates unnecessary blood pressure pulsation elements, or noise elements from the obstacle detection signals.

Furthermore, the second embodiment provides the following effects.

Since the pressure standard chambers S1, S2 are provided at the bottom side of the sensing portions 16, 17, it is not necessary to communicate back pressure to these portions from the outside the catheter. Therefore, a through hole in the seat 5 is not necessary. This simplifies the structure.

The pressure communicating hole 26 is sealed by the biocompatible silicone gel 9. Therefore, even if a sensor chip 6, which is not biocompatible, is used, biological substances such as blood do not come into direct contact with the sensor chip. This prevents the formation of thrombus that may be caused by such contact.

Furthermore, the same modifications described with regard to the first embodiment may be applied to the embodiment of FIG. 5.

What is claimed is:

1. A physical characteristic sensor used for detecting obstacles existing in a blood vessel and for detecting blood pressure, comprising:
   a hollow elongated support member, the support member having a longitudinal axis;
   a first sensing portion for detecting the obstacles;
   a second sensing portion for detecting the blood pressure, each said sensing portion extending in the longitudinal direction of the support member; said second sensing portion detecting blood pressure independently on said first sensing portion detecting obstacles and,
   a transmitting means for transmitting a physical quantity representative of at least one of the physical characteristics to each sensing portion, wherein the physical quantity acts on each sensing portion through said transmitting means in a direction that is generally perpendicular to the longitudinal axis.

2. The sensor as set forth in claim 1, further comprising a substantially rectangular sensor chip made of a semiconductor, wherein said sensing portions are arranged along a longitudinal direction of the sensor chip, said sensing portions separated by a predetermined interval.

3. The sensor as set forth in claim 2, wherein each sensing portion is formed thinner than the sensor chip by etching said sensor chip.

4. The sensor as set forth in claim 3, wherein said physical quantity is pressure, and wherein each sensing portion is provided with a strain gauge, said strain gauge varying in electric resistance value thereof in accordance with strain produced by said pressure applied to each sensing portion.

5. The sensor as set forth in claim 4, wherein:
   each sensing portion has a top surface and a bottom surface;
   said support member includes an opening located at the distal end thereof and first and second pressure communicating holes in a circumferential wall thereof, wherein the holes are respectively opposed to the top surfaces of said first and second sensing portions; and
   said transmitting means includes:
   a cap for closing the distal opening of the support member;
   a first silicone gel for transmitting the pressure acting on the cap to the bottom surface of the first sensing portion; and
   a second silicone gel arranged between the first and second through holes and the opposed top surfaces of the first and second sensing portions for transmitting the pressure about the support member to the top surfaces of the first and second sensing portions.

6. The sensor as set forth in claim 5 further comprising a first partition for blocking pressure communication between the top surface of said first sensing portion and said cap and a second partition for blocking pressure communication between the bottom surface of the first sensing portion and the rear surface of the second sensing portion.

7. A catheter used for detecting obstacles existing in a blood vessel and for detecting blood pressure, comprising:
   elongated catheter tube for insertion into a body, the tube having a longitudinal axis;
   a plurality of sensing portions arranged in the catheter tube to detect at least two physical characteristics acting on the catheter tube during insertion into the body, said plurality of sensing portions including a first sensing portion for detecting the obstacles and a second sensing portion for detecting the blood pressure, each sensing portion being arranged to extend in the longitudinal direction of the catheter tube; said second sensing portion detecting blood pressure independently on said first sensing portion detecting obstacles and
   a transmitting means for transmitting a pressure representing one of the two physical characteristics to each sensing portion, wherein the pressure acts through the transmitting means on each sensing portion in a direction that is perpendicular to the longitudinal axis of the catheter tube.

8. The sensor as set forth in claim 7, comprising a substantially rectangular sensor chip made of a semiconductor, wherein said sensing portion is arranged along a longitudinal direction of the sensor chip with a predetermined interval therebetween.

9. The catheter as set forth in claim 8 wherein each sensing portion is formed thinner than said sensor chip by etching the sensor chip.

10. The catheter as set-forth in claim 9 further comprising a seat for supporting said sensor chip.

11. The catheter as set forth in claim 9 wherein each sensing portion is provided with a strain gauge, said strain gauges varying in electric resistance value in accordance with strain produced by said pressures applied to each sensing portion.

12. The catheter as set forth in claim 11, wherein:

each sensing portion has a top surface and a bottom surface;

said catheter tube includes an opening located at the distal end thereof, and first and second pressure communicating holes provided in a circumferential wall thereof and respectively opposed to the top surfaces of said first and second sensing portions; and said transmitting means includes:

a cap for closing the distal opening;

said seat having a through hole opposed to the rear surface of the first sensing portion;

a first silicone gel for transmitting pressure acting on said cap to the bottom surface of said first sensing portion through the through hole of said seat; and a second silicone gel arranged between the first and second pressure communicating holes and the top surfaces of said first and second sensing portions for transmitting a pressure representing the blood pressure about the catheter tube to the top surfaces of the first and second sensing portions.

13. The catheter as set forth in claim 12 further comprising a first partition for blocking pressure communication between the top surface of said first sensing portion and said cap, and a second partition for blocking pressure communication between the bottom surface of said first sensing portion and the rear surface of said second sensing portion.

14. The catheter as set forth in claim 11, wherein:

said catheter tube includes an opening located at the distal end thereof and a pressure communicating hole provided in a circumferential wall thereof, wherein said pressure communicating hole is opposed to the top surface of said second sensing portion; and said transmitting means includes:

a cap for closing the distal opening of the tube, pressure chambers located adjacent to the bottom surfaces of said first and second sensing portions;

a first silicone gel for transmitting pressure representing forces acting on said cap to the top surface of said first sensing portion; and a second silicone gel arranged between said pressure communicating hole and the opposed top surface of said second sensing portion for transmitting a pressure representing the pressure acting about said catheter tube to the top surface of the second sensing portion.

15. The catheter as set forth in claim 14 including a partition for blocking pressure communication between the top surface of said first sensing portion and the top surface of said second sensing portion.

* * * * *